(12) United States Patent
Matsumoto

(10) Patent No.: US 6,273,565 B1
(45) Date of Patent: Aug. 14, 2001

(54) OPHTHALMOLOGICAL DEVICE

(75) Inventor: Kazuhiro Matsumoto, Yono (JP)

(73) Assignee: Canon Kabushiki Kaisha, Toko (JP)

( * ) Notice: Subject to any disclaimer, the term of this patent is extended or adjusted under 35 U.S.C. 154(b) by 0 days.

(21) Appl. No.: 09/161,373

(22) Filed: Sep. 28, 1998

(30) Foreign Application Priority Data

Oct. 3, 1997 (JP) .................................................. 9-287909

(51) Int. Cl.$^7$ ........................................................ A61B 3/14
(52) U.S. Cl. ............................................................ 351/210
(58) Field of Search .................................... 351/204, 205, 351/209, 210, 211, 212, 221, 246, 206

(56) References Cited

U.S. PATENT DOCUMENTS

| | | |
|---|---|---|
| 4,820,037 | 4/1989 | Kohayakawa et al. . |
| 4,848,896 | 7/1989 | Matsumoto . |
| 4,952,049 | 8/1990 | Matsumoto . |
| 5,233,372 | 8/1993 | Matsumoto . |
| 5,455,644 | 10/1995 | Yazawa et al. . |
| 5,847,805 | 12/1998 | Kohayakawa et al. . |
| 5,946,075 | * 8/1999 | Horn ..................................... 351/246 |

\* cited by examiner

*Primary Examiner*—George Manuel
(74) *Attorney, Agent, or Firm*—Fitzpatrick, Cella, Harper & Scinto

(57) ABSTRACT

An ophthalmological device in which a liquid crystal element is controlled such that four liquid crystal element cells, with an eye fixation target at the center of the four cells, are set in a transmissive state, while the rest of the cells are set in a non-transmissive state. In this manner, an eye fixation target is shown. In particular, an opthalmological device in which, when a photographer presses an eye fixation target enhancing switch, the four cells at each of the upper right, lower right, lower left, and upper left side of the eye fixation target center are successively set in a transmissive and a non-transmissive state. As a result, the eye fixation target appears, to the subject, to rotate around the eye fixation target center. This rotation appearance attracts the attention of the subject, allowing him to easily find the eye fixation target, and properly view the eye fixation target within a short time.

17 Claims, 6 Drawing Sheets

OPHTHALMOLOGICAL DEVICE

BACKGROUND OF THE INVENTION

1. Field of the Invention

The present invention relates to an ophthalmological device, such as a fundus camera for use in an ophthalmic hospital or the like.

2. Description of the Related Art

Eye fixation lamps in conventional fundus cameras are designed to allow a desired eye fixation target to be shown within any location in a field of view of, for example, a subject whose eye is being examined. When such conventional fundus cameras are used in examining a subject having a cataract or an abnormal eye caused by opacity of the light-projecting section, the photographer uses a means designed to change the location of the eye fixation target displayed in the camera. Since the means can be used to change the location of the displayed target in very small amounts, the means is useful in helping the subject easily find the eye fixation target.

However, the above-described conventional ophthalmological device has the following problems:

(1) When the location of the displayed eye fixation target is changed, the body of the device is also moved, causing the opthalmological device and the eye of the subject to become misaligned;

(2) The photographer cannot concentrate on aligning the opthalmological device and the subject's eye while changing the location of the eye fixation target being displayed, so that it takes more time to take photographs;

(3) When the eye fixation light is moved in small amounts to allow the subject to easily find the eye fixation target, reproducibility of the location of the eye fixation target is reduced, thereby preventing photographs of a fixed range from being taken.

SUMMARY OF THE INVENTION

Accordingly, in order to overcome the aforementioned problems, it is an object of the present invention to provide an ophthalmological device which allows a subject to easily find the desired eye fixation target and allows photographs to be taken within a shorter time.

To this end, according to one aspect of the present invention, there is provided an ophthalmological device comprising an eye fixation target for guiding a subject's eye; and control means for performing a controlling operation that can change the shape or the location of a pattern of the eye fixation target, with respect to virtually a point as center.

According to another aspect of the present invention, there is provided an ophthalmological device comprising a eye fixation target for guiding a subject's eye; and control means for changing the shape or the location of a pattern of the eye fixation target with respect to virtually a point as after the eye fixation target has described a certain path.

DESCRIPTION OF THE PREFERRED EMBODIMENT

A description will now be given of an embodiment of the present invention, with reference to the drawings.

Figure 1:
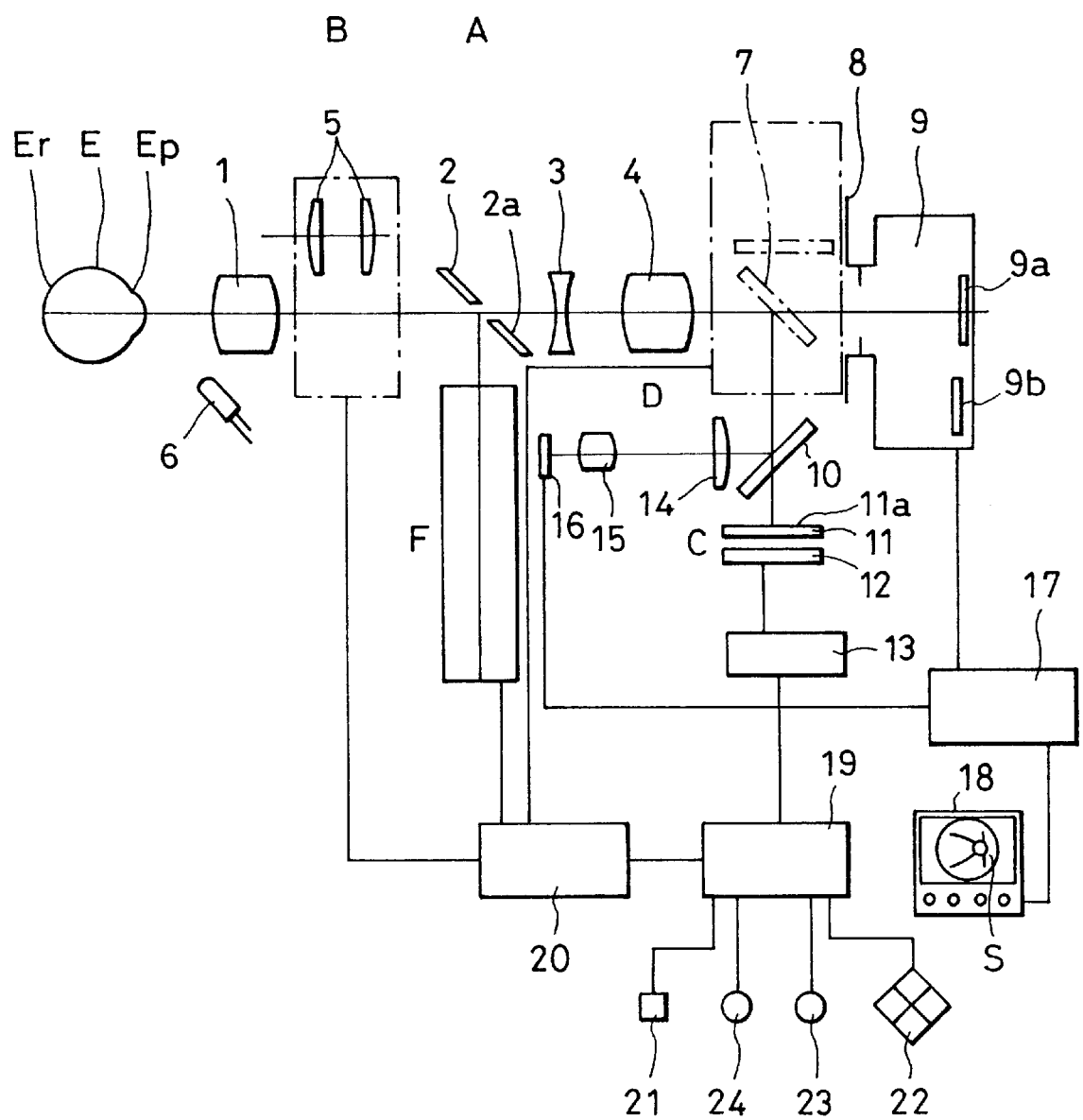
FIG. 1 is a view of the construction of an embodiment of the fundus camera in accordance with the present invention.

FIG. 1 is a view of the construction of an embodiment of the fundus camera. Referring to FIG. 1, the fundus photographic optical system A comprises an objective lens 1, a mirror 2 with an aperture 2a, a focusing lens 3 which moves towards an optical axis for performing focusing operations, and a photographic lens 4. The mirror 2, the focusing lens 3, and the photographic lens 4 are disposed along the optical axis and behind the objective lens 1 that faces an eye E examined. The front eye portion viewing optical system B comprises a lens group 5, which can be moved in and out of an optical path between the objective lens 1 and the mirror 2, and a front eye portion illuminating light source 6, which is disposed near the objective lens 1. Behind the photographic lens 4 are disposed a change-over mirror 7, a mount 8, and a digital camera 9 that has an image-forming surface 9a and incorporates an image memory 9b.

The eye fixation target showing means C, shown in FIG. 1, comprises a half mirror 10, a transmissive liquid crystal element 11, and a backlight 12. The half mirror 10 is disposed in a direction in which light beams are reflected from the change-over mirror 7, and the liquid crystal element 11 is disposed on an optical path extending in a direction in which light beams are transmitted through the half mirror 10. In the liquid crystal element 11, disposed a plurality of cells consisting of liquid crystals disposed in a matrix arrangement. The liquid crystal element 11 is connected to an output of a liquid crystal controlling means 13 for controlling the on and off states of each of the cells, so that light beams may or may not be allowed to pass therethrough. The fundus viewing means D comprises a lens 14, a photographic lens 15, and an image-forming means 16, all of which are disposed along an optical path extending in a direction in which light beams are reflected from the half mirror 10. The fundus illuminating means F, which is of an ordinary type, is disposed in a direction in which light beams are incident upon the mirror 2. The fundus illuminating means F steadily emits infrared rays, and emits visible light rays when photographs are being taken.

An output of the digital camera 9 and an output of the image-forming means 16 are connected to an image processing section 17 whose output is connected to a monitor 18. Outputs of a central processing unit (CPU) 19 are connected to the liquid crystal control means 13 and a control means 20. An output of the control means 20 is connected to the lens group 5 of the front eye portion viewing optical system B, the change-over mirror 7, and the fundus illuminating means F. To the CPU 19 are connected an output of a viewing portion selection switch 21, an eye fixation target moving switch 22, an eye fixation target enhancing switch 23, and a photographic switch 24.

In the ophthalmological device having the above-described construction, while viewing the front eye portion of a subject, the photographer aligns the fundus photographic optical system A and an eye E examined. This alignment is such that an optical axis of the fundus photographic optical system A passes through the center of a pupil Ep of the eye E examined. The objective lens 1 and the cornea of the eye E being examined, are kept at a proper distance from each other. When the front eye portion is being viewed, the lens group 5 of the front eye portion viewing optical system B is inserted into a photographic optical path, and light beams, emitted from the front eye portion illuminating light source 6, illuminate the front eye portion of the subject, such as the eyelid of the eye E being examined, or parts near the eyelid (for example, the iris or the sclera). The light beams, which have illuminated the front eye portion, cause an image of the front eye portion to be formed. These light beams, carrying the front eye portion image, pass through the objective lens 1, the lens group 5, the photographic aperture 2a, the focusing lens 3, and the lens 4. Then, they are reflected downward by the change-over mirror 7, and then towards the left by the half mirror 10 in order to form an image again near the lens 14. Afterwards, the light beams, carrying the image formed near the lens 14, pass through the photographic lens 15 that cause an image to be formed near the image-forming means 16. The image-forming means 16 converts the image of the front eye portion, formed near the image-forming means 16, into an image signal which is input into the image processing section 17. The image processing section 17 processes the image signal for displaying the image of the front eye portion on a monitor 18.

When the viewing portion selecting switch 21 is operated after alignment of the objective lens 1 and the eye E being examined, the CPU 19 detects this switch operation, causing the control means 20 to turn off the front eye portion illuminating light source 6 and the front eye portion viewing optical system B to move out of the photographic optical path. The CPU 19 causes the backlight 12, through the liquid crystal control means 13, to be turned on. The backlight 12 illuminates the liquid crystal element 11 in such a manner that only predetermined cells allow transmission of light in order to display an eye fixation target 11a pattern. Then, the fundus illuminating means F emits infrared rays which steadily illuminate a fundus Er.

The infrared rays, which have illuminated the fundus Er, form an image thereof. These infrared rays, carrying the fundus image, pass through the pupil Ep, the objective lens 1, the photographic aperture 2a of the mirror 2, the focusing lens 3, and the photographic lens 4. They are then reflected downward by the change-over mirror 7, and strike the half mirror 10, which reflect the infrared rays towards the left in order to form an image again near the lens 14. Afterwards, the infrared rays, carrying the image formed near the lens 14, causes an image to be formed near the image-forming means 16. Similar to the image of the front eye portion, the fundus image of the fundus is converted into an image signal which passes through the image processing section, which processes the image signal for displaying the fundus image on the monitor 18. The photographer examines the fundus image on the monitor 18, checks the portion of the eye to be photographed and the focusing condition of the ophthalmological device, and checks for possible flares.

The image processing section 17 causes a character S, which indicates the location of the eye fixation target 11a pattern to the subject, to be combined with the image of the fundus and to be displayed on the monitor 18. When the photographer, while observing the image of the fundus of the subject, operates the eye fixation target moving switch 22, in order to photograph the desired portion of the eye, the photographer can guide the subject's eye so that it is fixed upon the eye fixation target 11a pattern.

Figure 2:
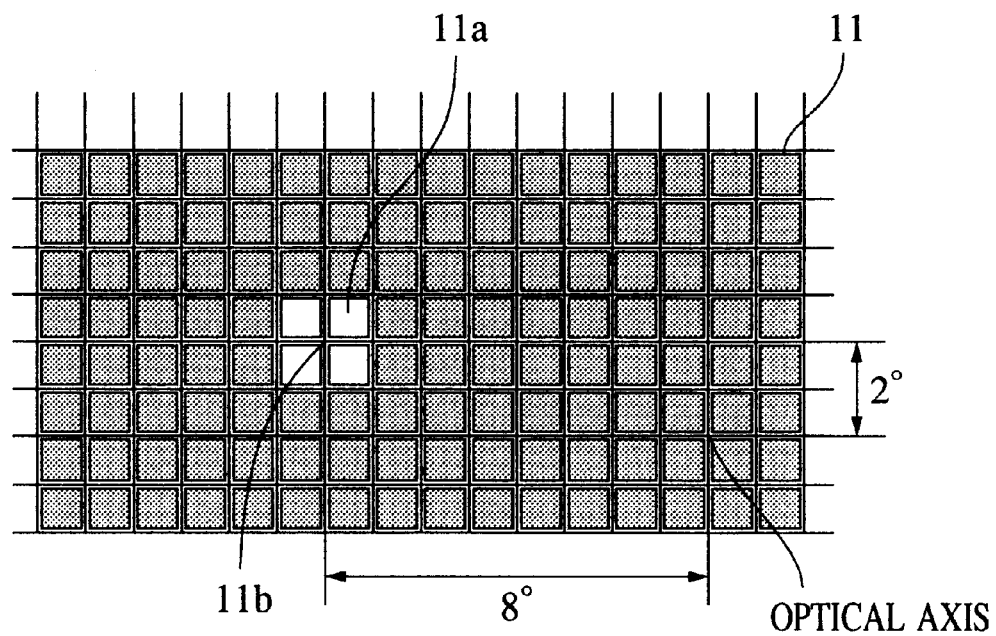
FIG. 2 is a view illustrating a liquid crystal element.

In giving eye examinations to different individuals, an eye fixation light is used to guide each subject's eye so that it is fixed upon a particular location such that the center of the optic disc and the macula of the eye E being examined, coincides with the center of the image, as shown in FIG. 2. Although there are differences among individuals, the optic disc is frequently displaced slightly above the macula, so that the optic disc and the macula are seldom found on the same horizontal line. Therefore, as viewed from the subject, it is necessary to show the eye fixation target 11a pattern at a location about two degrees upwards and about eight degrees leftwards from the optical axis. This can be achieved by controlling the cells of the liquid crystal element 11 such that the four cells, located around a eye fixation target center 11b and found two degrees upward and eight degrees leftwards from the optical axis, are set in a transmissive state and such that the rest of the cells are set in a non-transmissive state, as shown in FIG. 2.

When the subject has a cataract or the like, or the subject can see, for example, other known focusing targets (not shown), merely showing the eye fixation target 11a pattern at the aforementioned location may not allow the subject to easily find the eye fixation target 11a pattern. This can be determined when the location of the macula and the location of the character S do not match.

Figure 3:
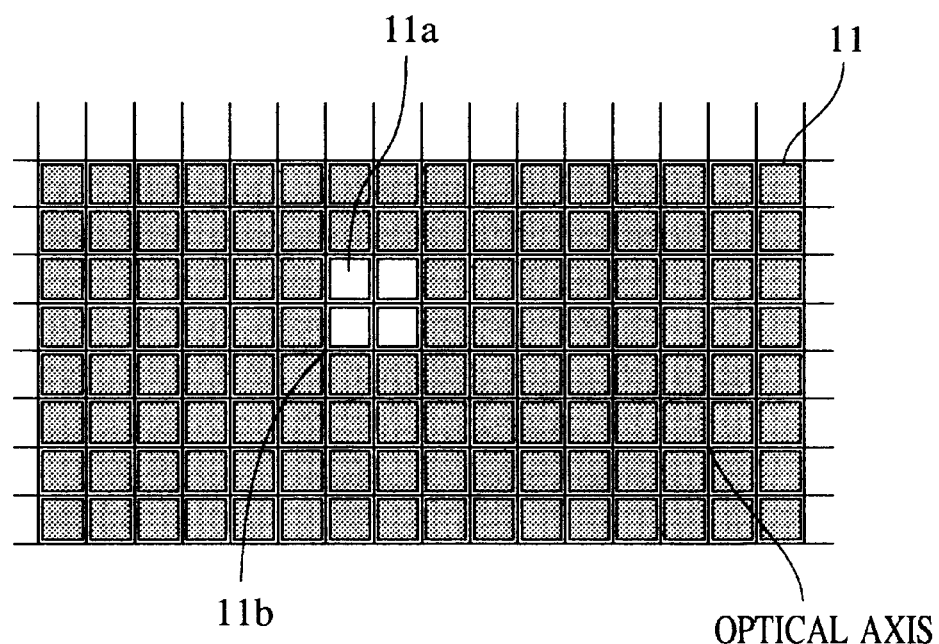
FIG. 3 is a view illustrating the liquid crystal element.
Figure 4:
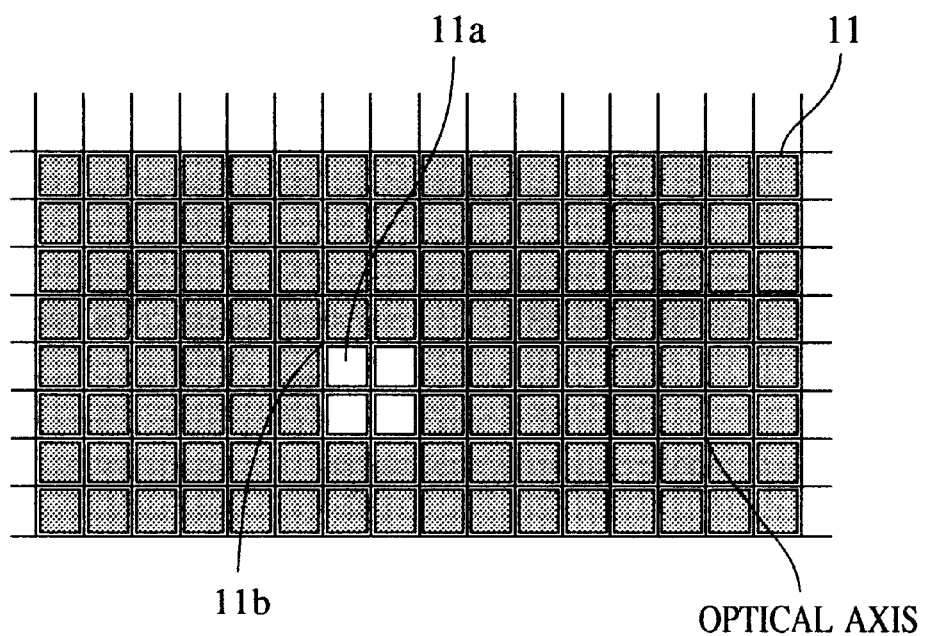
FIG. 4 is a view illustrating the liquid crystal element.
Figure 5:
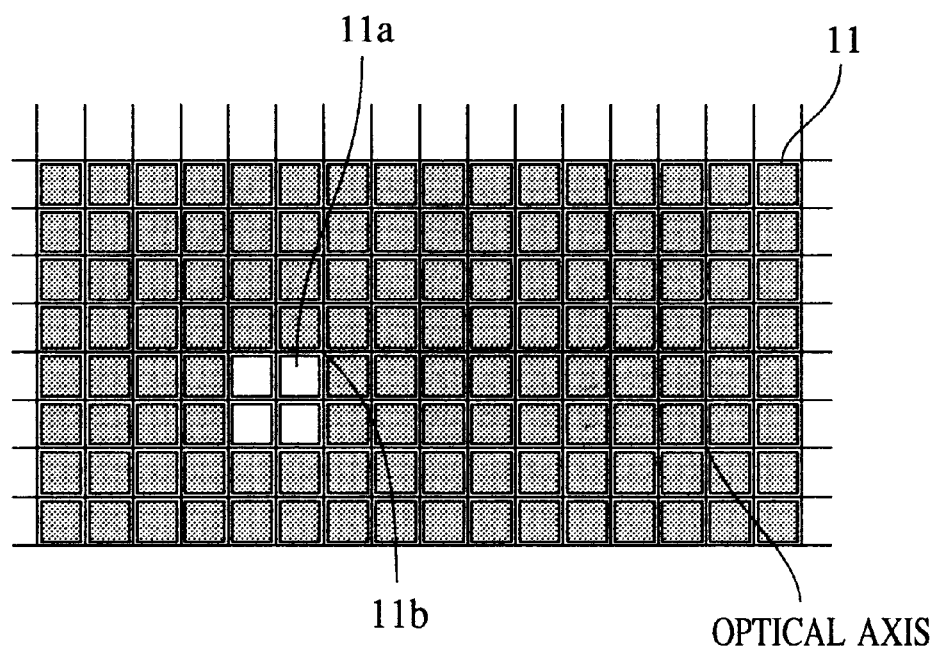
FIG. 5 is a view illustrating the liquid crystal element.
Figure 6:
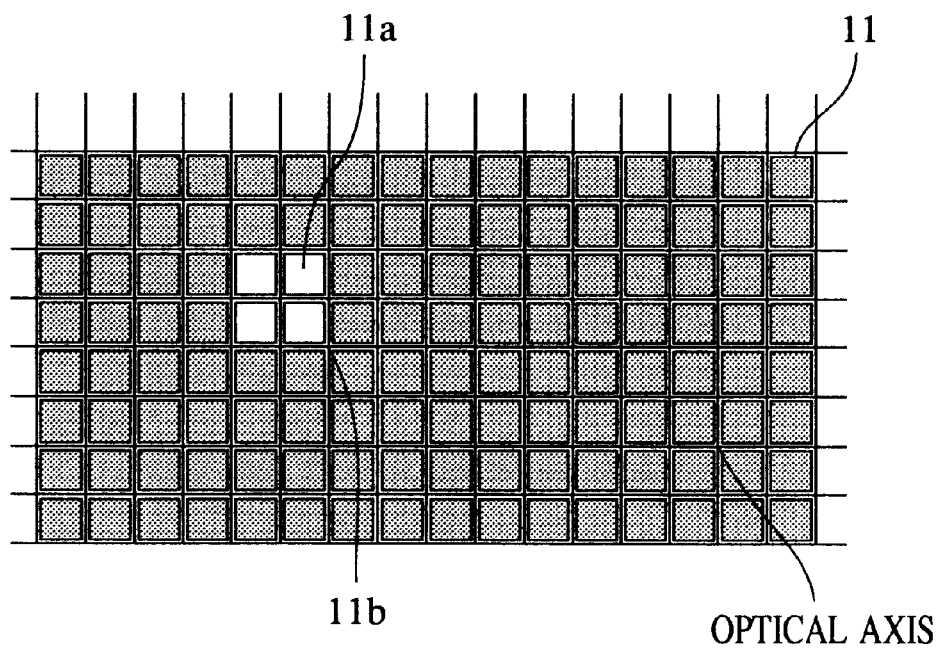
FIG. 6 is a view illustrating the liquid crystal element.

In such a case, the photographer operates the eye fixation target enhancing switch 23 in order to cause the liquid crystal control means 13 to control the liquid crystal element 11 in such a manner that the cells around the eye fixation target center 11b are successively and repeatedly set in a transmissive state. First, as shown in FIG. 3, only the cell at the upper right side of the eye fixation target center 11b is set in a transmissive state, with the transmissive state of the cell at the upper right side being called a first transmissive state. Then, as shown in FIG. 4, only the cell at the lower right side of the eye fixation target center 11b is set in a transmissive state, with the transmissive state of the cell at the lower right side being called a second transmissive state. Then, as shown in FIG. 5, only the cell at the lower left side of the eye fixation target center 11b is set in a transmissive state, with the transmissive state of the cell at the lower left side being called a third transmissive state. Then, as shown in FIG. 6, only the cell at the upper left side of the eye fixation target center 11b is set in a transmissive state, with the transmissive state of the cell at the upper left side being called a fourth transmissive state. Thereafter, the whole cycle is repeated. Accordingly, only when the eye fixation target enhancing switch 23 is being pressed does the subject sees the fixed target 11a pattern rotating around the eye fixation target center 11b, thereby drawing the attention of the subject and allowing him to easily find the eye fixation target 11a pattern and properly fix his eye upon the desired location within a short time.

After obtaining the desired portion of the eye to be photographed by the above-described operations, the fundus of the subject's eye is photographed by operating the photographic switch 24. When the photographic switch 24 is operated, the control section 19 causes the change-over mirror 7 to move out of an optical path. The digital camera 9 starts to store light to photograph still pictures, and, at the same time, the fundus illuminating means F emits flashes of visible light beams, which are reflected by the mirror 2 and pass through the objective lens 1 in order to illuminate the fundus Er.

The light beams, which have illuminated the fundus Er, cause an fundus image to be formed. The light beams pass through the objective lens 1, the photographic aperture 2a in the mirror 2, and the lenses 3 and 4, and form an image on the image-forming surface 9a of the digital camera 9. The image is converted into digital signals, and stored in digital form in the image memory 9b in the digital camera 9, whereby the fundus is photographed. At the same time, the image is converted into video signals and reproduced at the monitor 18. Here, the character S, which indicates the location of the eye fixation target, is not shown.

Figure 7:
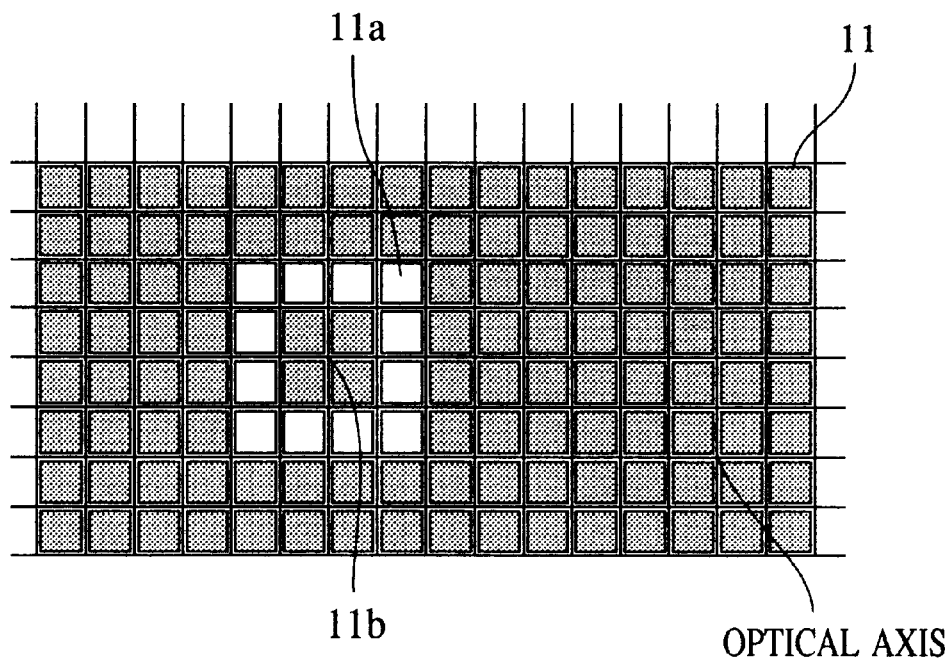
FIG. 7 is a view illustrating the liquid crystal element.

In this embodiment, the location of the eye fixation target 11a pattern is enhanced by controlling the liquid crystal element, so that the eye fixation target 11a pattern appears to rotate as viewed by the subject. Other methods, however, may also be used in order to accomplish the same purpose. For example, the cells, which are formed around the eye fixation target 11a pattern of FIG. 4, may be set in a transmissive state so as to form a pattern therearound, with the eye fixation target center 11b being the center of the pattern, as shown in FIG. 7. In another example, the eye fixation target 11a pattern of FIG. 4 and the pattern of FIG. 7 may be alternately displayed to enhance the location of the eye fixation target 11a pattern.

Figure 8:
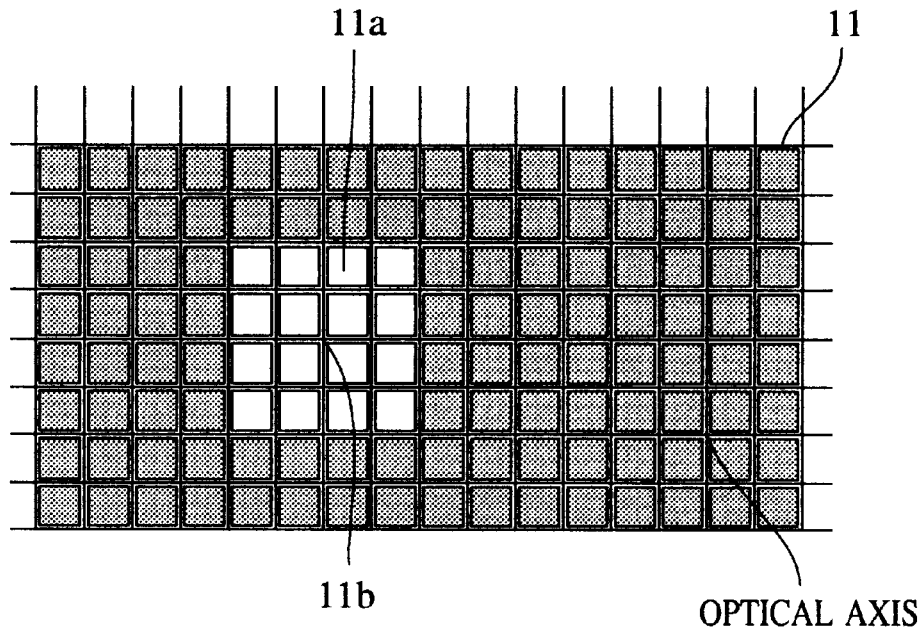
FIG. 8 is a view illustrating the liquid crystal element.
Figure 9:
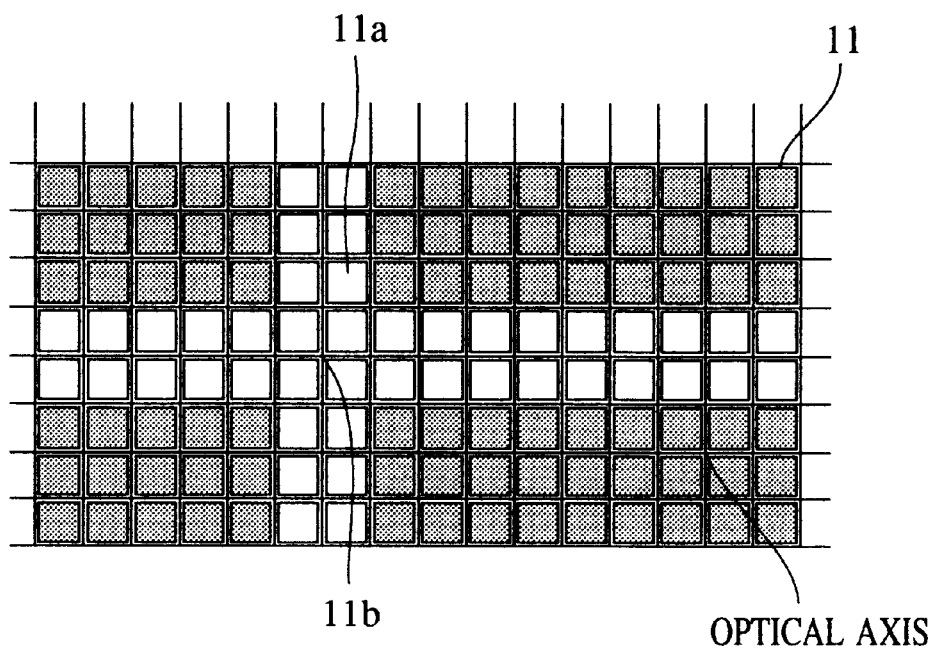
FIG. 9 is a view illustrating the liquid crystal element.

In still another method, the eye fixation target 11a pattern may be enhanced by alternately displaying the pattern of FIG. 4 and a pattern, shown in FIG. 8, which is similar in shape but larger in size. Further, the eye fixation target 11a pattern may be enhanced by displaying a cross whose lines intersect at the eye fixation target center 11b, in order to guide the subject's eye so that it is fixed upon the eye fixation target 11a pattern. In this case, a larger cross is more likely to be in the subject's field of view. Therefore, when a larger cross is used, the subject's eye can be guided so that it is fixed upon the eye fixation target 11a pattern with greater efficiency. It is to be noted that the pattern of FIG. 4 and the pattern of FIG. 9 can be alternately displayed.

As the displayed pattern is changed, the brightness of the backlight 12 or the open time of the liquid crystal element 11, for example, may be changed to vary the apparent brightness as viewed by the viewer, thereby drawing the attention of the viewer very efficiently. In addition, the location of the eye fixation target 11a pattern can be enhanced by successively displaying a plurality of patterns with respect to a virtual common center.

Although in the embodiment the character S, which indicates the location of the eye fixation target 11a pattern, is not displayed during reproduction of the still picture after it has been photographed, the character S can be kept on the display. When it is kept on the display, the subject can accurately know the location of the eye fixation target 11a pattern. In addition, the character S can be used when conducting tests to determine whether or not the desired location is being viewed eccentrically. Here, when the character S is such that it can be switched between a display state and a non-display state, operating the eye fixation target enhancing switch 23 during still picture reproduction allows confirmation of the location of the eye fixation target 11a pattern, as required, thereby making it easier to operate the ophthalmological device.

In the above-described embodiment, although the eye fixation target pattern was changed so as to draw the attention of the subject by operating the eye fixation target enhancing switch 23, the eye fixation target pattern can be changed for a certain period of time by operating the observing portion selecting switch 21. This allows the subject to immediately find the displayed eye fixation target 11a pattern without operating other switches. Hence, the photographer can take photographs more efficiently and make settings that suit him, thereby making the ophthalmological device very handy.

Although the displayed pattern is changed only when the eye fixation target enhancing switch 23 is being pressed, it is possible to change the eye fixation target 11a pattern for a certain predetermined length time from the time of operates the eye fixation target enhancing switch 23. In this case, the photographer can concentrate on alignment operations during the predetermined length of time, thereby allowing the photographer to take photographs even more efficiently.

In the case where photographs have been taken within a certain period of time, it is preferable to return the display back to that showing the usual eye fixation target 11a pattern after picture-taking, since this allows the next picture to be taken more efficiently. Continuously changing the eye fixation target pattern, or the like, during the time from the input operation of the eye fixation target enhancing switch 23 to the completion of the picture-taking is particularly effective when examining people with low visual recognition capacity.

It is also possible to draw the attention of the subject when the backlight 12 is composed of light-emitting diodes (LEDs) which emit different colors, and the colors of the light-emitting diodes are successively switched in synchronism with changes in the eye fixation target pattern. In addition, photographs can be taken more efficiently by changing the location of the eye fixation target 11a pattern and enhancing the location of the eye fixation target 11a pattern by a simple operation with one hand. This can be achieved by providing a switch which, after detection of the direction in which the eye fixation target moving switch 22 has been pushed downward, is used to move the eye fixation target 11a pattern in the detected direction. This switch serves as eye fixation target enhancing switch 23. A pushbutton switch is provided at the top portion of the switch used to move the eye fixation target 11a pattern.

Figure 10:
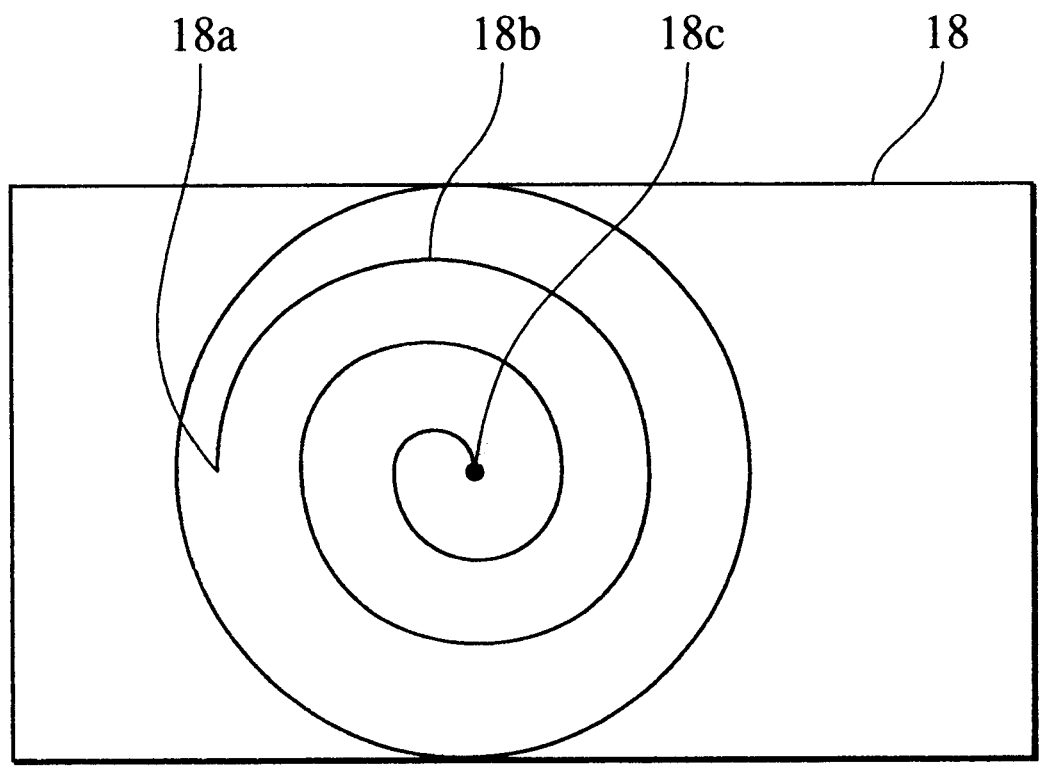
FIG. 10 is a view illustrating the movement of the eye fixation target.

Although in the above-described embodiment, in order to guide the subject's eye so that it is fixed upon a desired location, an ophthalmologist changes the location or the shape of a target pattern by pressing a switch, it may also be done as illustrated in FIG. 10. In this method, the ophthalmologist presses a switch to control the movement of a pattern in such a manner that starting from a starting point 18a on the monitor 18 the pattern moves so as to describe a fixed path 18b and eventually converge on an eye fixation target center 18c. Since the ophthalmologist does not know where the subject is viewing, this method allows the ophthalmologist to guide the subject's eye so that it is fixed upon a desired location more efficiently, as a result of increasing the probability with which the eye fixation target 11a pattern passes near the line of sight of the subject by moving the eye fixation target pattern so as to describe a path. It is to be noted that although the starting point 18a of the path was at the center of the monitor 18, it may be placed at any location that makes the opthalmological device easier to use.

The subject's eye can be guided so that it is fixed upon a desired location even more efficiently by a method which uses a position detecting means, such as a touch panel, provided on the monitor 18. In this method, when the ophthalmologist inputs the location of the subject's macula, displayed on the monitor 18, and the path is started from near the subject's macula in order to guide the subject's eye so that it is fixed upon the desired eye fixation target, the opthalmologist can directly guide the subject's eye so that it is fixed upon the desired eye fixation target.

As can be understood from the foregoing description, according to the opthalmological device of the present invention, by changing the shape or the location of the eye fixation pattern with respect to virtually a point as center, the subject's eye can be reliably guided so that it is precisely fixed upon the eye fixation target, the time taken for the subject to view the eye fixation target can be reduced, and pictures can be taken more efficiently.

What is claimed is:

1. An ophthalmological device, comprising:

an eye fixation target system for guiding a subject's eye;

means for photographing the subject's eye fundus; and control means for changing at least one of the shape and the location of a pattern of said eye fixation target with respect to an eye fixation target center before said photographing means photographs the subject's eye to guide the subject's eye to the eye fixation target pattern more easily than using a fixed eye fixation target pattern before photographing.

2. An ophthalmological device according to claim 1, further comprising input means for giving commands to operate said control means.

3. An ophthalmological device according to claim 2, wherein said control means performs a controlling operation such that the shape or the location of said eye fixation target is changed for a certain period of time from the time of input to said input means.

4. An ophthalmological device according to claim 3, wherein said control means performs a controlling operation such that the changing of the shape or the location of the pattern of said eye fixation target ends upon starting of a photographic operation.

5. An ophthalmological device, comprising:

an eye fixation target pattern system for guiding a subject's eye;

means for photographing the subject's eye fundus; and control means for causing the eye fixation target pattern to move on a fixed path to eventually converge on an eye fixation target center before said photographing means photographs the subject's eye fundus to guide the subject's eye to the eye fixation target pattern more easily than using a fixed eye fixation target pattern before photographing.

6. An ophthalmological device, comprising:

an eye fixation target pattern system for guiding a subject's eye;

means for photographing the subject's eye fundus; and control means for successively and repeatedly changing the location of said eye fixation target pattern with respect to an eye fixation target center before said photographing means photographs the subject's eye to guide the subject's eye to the eye fixation target pattern more easily than using a fixed eye fixation target pattern before photographing.

7. An ophthalmological photographing device, comprising:

an eye fixation target system indicating a target pattern for guiding a subject's eye;

an operation device;

a photographing device configured and positioned to photograph the subject's eye; and a controller for controlling said eye fixation target system in response to operation of said operation device so as to change successively and repeatedly the indicated target pattern with respect to an eye fixation target center before said photographing device photographs the subject's eye.

8. A device according to claim 7, wherein said target pattern is movable, wherein said eye fixation target indicator comprises a display for displaying the movable target pattern.

9. A device according to claim 8, wherein said display comprises a liquid crystal element.

10. A device according to claim 10, further comprising a monitor device displaying an image of said subject's eye with the target pattern at least during operation of said operation device.

11. A device according to claim 10, wherein said photographing system comprises a digital camera.

12. An opthalmological photographing device, comprising:

a photographing system configured to photograph the subject's eye;

an eye fixation target system for guiding a subject's eye, including a controller and a display on which a target pattern is indicated, before said photographing system photographs the subject's eye;

a first operation device electrically connected to the controller, wherein the controller controls movements of the target pattern on the display in response to operation of the first operation device; and a second operation device electrically connected to the controller, wherein the controller controls indication enhancement of the target pattern on the display in response to operation of the second operation device.

13. A device according to claim 12, wherein said display comprises a liquid crystal element.

14. A device according to claim 12, further comprising a monitor device displaying an image of said subject's eye with the target pattern at least during operations of said first and second operation devices.

15. A device according to claim 12, further comprising a third operation device electrically connected to the controller, wherein the controller controls the photographing system to take a photograph of the subject's eye.

16. A device according to claim 15, wherein said photographing system comprises a digital camera.

17. A device according to claim 16, further comprising a monitor device displaying an image of said subject's eye with the target pattern at least during operations of said first and second operation devices.

* * * * *

UNITED STATES PATENT AND TRADEMARK OFFICE
CERTIFICATE OF CORRECTION

PATENT NO.    : 6,273,565 B1
DATED         : August 14, 2001
INVENTOR(S)   : Kazuhiro Matsumoto It is certified that error appears in the above-identified patent and that said Letters Patent is hereby corrected as shown below:

Title page,
Item [73], Assignee: "Toko" should read -- Tokyo --.

Column 1,
Line 53, "a" should read -- an --.
Line 56, "as" should be deleted.

Column 2,
Line 20, "E" should read -- E being --.
Line 36, "11," should read -- 11, are --.
Line 67, "E" should read -- E being --.

Column 3,
Line 3, "E" should read -- E being --.
Line 20, "cause" should read -- causes --.
Line 49, "causes" should read -- cause --.
Line 50, "Similar" should read -- Similarly --.
Line 51, "of the fundus" should be deleted.

Column 4,
Line 13, "a" should read -- an --.
Line 66, "an" should read -- a --.

Column 6,
Line 6, "length time from the time of" should read -- length of time after the photographer --.

UNITED STATES PATENT AND TRADEMARK OFFICE
CERTIFICATE OF CORRECTION

PATENT NO. : 6,273,565 B1
DATED : August 14, 2001
INVENTOR(S) : Kazuhiro Matsumoto It is certified that error appears in the above-identified patent and that said Letters Patent is hereby corrected as shown below:

Column 8,
Line 17, "claim 10," should read -- claim 7, --.
Line 22, "system" should read -- device --.

Signed and Sealed this

Nineteenth Day of November, 2002

Attest:

Attesting Officer

JAMES E. ROGAN
Director of the United States Patent and Trademark Office